(12) United States Patent
Bar-Cohen et al.

(10) Patent No.: US 12,390,619 B2
(45) Date of Patent: *Aug. 19, 2025

(54) SHEATH FOR MAINTAINING POSITION IN A BODY CAVITY

(71) Applicants: CHILDREN'S HOSPITAL LOS ANGELES, Los Angeles, CA (US); UNIVERSITY OF SOUTHERN CALIFORNIA, Los Angeles, CA (US)

(72) Inventors: Yaniv Bar-Cohen, South Pasadena, CA (US); Gerald Loeb, South Pasadena, CA (US)

(73) Assignees: CHILDREN'S HOSPITAL LOS ANGELES, Los Angeles, CA (US); UNIVERSITY OF SOUTHERN CALIFORNIA, Los Angeles, CA (US)

( * ) Notice: Subject to any disclaimer, the term of this patent is extended or adjusted under 35 U.S.C. 154(b) by 221 days.

This patent is subject to a terminal disclaimer.

(21) Appl. No.: 17/903,961

(22) Filed: Sep. 6, 2022

(65) Prior Publication Data

US 2022/0409865 A1 Dec. 29, 2022

Related U.S. Application Data

(63) Continuation of application No. 15/552,250, filed as application No. PCT/US2016/018907 on Feb. 22, 2016, now Pat. No. 11,433,222.

(60) Provisional application No. 62/118,892, filed on Feb. 20, 2015.

(51) Int. Cl.
*A61M 25/06* (2006.01)
*A61B 17/34* (2006.01)
*A61M 25/04* (2006.01)
*A61N 1/362* (2006.01)
*A61N 1/372* (2006.01)

(52) U.S. Cl.
CPC ..... *A61M 25/0662* (2013.01); *A61B 17/3421* (2013.01); *A61M 25/04* (2013.01); *A61N 1/362* (2013.01); *A61N 1/37205* (2013.01); *A61B 17/3478* (2013.01); *A61B 2017/3484* (2013.01); *A61B 2017/3488* (2013.01); *A61M 2205/0266* (2013.01); *A61M 2210/122* (2013.01)

(58) Field of Classification Search
CPC .............. A61M 25/04; A61M 25/0082; A61M 25/0662; A61M 2025/0687; A61M 2025/0293
See application file for complete search history.

(56) References Cited

U.S. PATENT DOCUMENTS

| | | | |
|---|---|---|---|
| 5,509,900 A * | 4/1996 | Kirkman | A61M 25/04 606/198 |
| 5,573,008 A | 11/1996 | Robinson et al. | |
| 7,651,503 B1 | 1/2010 | Coe et al. | |
| 7,931,658 B2 * | 4/2011 | Rosenberg | A61M 25/04 606/108 |
| 2001/0004699 A1 | 6/2001 | Gittings et al. | |
| 2002/0091398 A1 | 7/2002 | Galdonik et al. | |

(Continued)

*Primary Examiner* — Diane D Yabut
(74) *Attorney, Agent, or Firm* — NovoTechIP International PLLC

(57) ABSTRACT

The present invention provides a novel design for sheaths intended for medical procedures. The sheath includes structures that anchor the sheath in a cavity or space when deployed but are at the same time retractable such that the sheath can be removed without tearing the tissue defining the space.

16 Claims, 10 Drawing Sheets

(56) References Cited

U.S. PATENT DOCUMENTS

| | | |
|---|---|---|
| 2002/0151913 A1 | 10/2002 | Berg et al. |
| 2006/0116625 A1 | 6/2006 | Renati et al. |
| 2008/0306467 A1* | 12/2008 | Reydel .............. A61M 25/0068 604/523 |
| 2009/0230167 A1* | 9/2009 | Xiao .................... A61M 25/04 227/175.1 |
| 2011/0098720 A1 | 4/2011 | Taylor et al. |
| 2012/0004589 A1 | 1/2012 | Rapacki et al. |
| 2014/0257240 A1 | 9/2014 | Burdulis |
| 2015/0250991 A1* | 9/2015 | Silvestro ................ A61B 17/22 606/194 |

* cited by examiner

SHEATH FOR MAINTAINING POSITION IN A BODY CAVITY

This patent application is a continuation of U.S. patent application Ser. No. 15/552,250, filed Aug. 18, 2017, now U.S. Pat. No. 11,433,222; which is a 371 national stage application of PCT/US2016/018,907, filed Feb. 22, 2016; which claims priority to U.S. Provisional Patent Application Ser. No. 62/118,892, filed Feb. 20, 2015; the contents of which are hereby incorporated by reference herein in their entirety into this disclosure.

BACKGROUND OF THE INVENTION

Field of the Invention

The present invention relates to the field of medical devices. More specifically, the invention relates to sheaths for use in procedures that involve performing medical procedures, such as placing medical devices in a body cavity, such as a pericardial sac.

Description of Related Art

Pericardial procedures have become commonplace in many hospitals. In these procedures, a sheath is placed into the pericardial space and subsequent procedures (including epicardial ablations and placement of left atrial occlusion devices) are performed by inserting catheters or implantation equipment through the sheath. Likewise, in the past few years new designs for micropacemakers and devices for delivering them to the epicardial tissue of a heart have been developed.

For example, U.S. patent application publication number 2012/0078267 discloses a fully intrathoracic artificial pacemaker. The pacemaker is of sufficiently compact size to allow for implantation of both the electrode and the power source within the chest cavity. In exemplary embodiments, a screw-type electrode is used for connection to heart tissue, and a relatively short lead is used to connect the electrode to a battery unit, which can comprise electronics for control of the pacemaker. An assembly for implanting the pacemaker, as well as methods of implanting the pacemaker, are also disclosed.

In addition, PCT publication WO 2013152259 discloses a fully implantable cardiac pacemaker system. The pacemaker system includes a pacemaker having an electrode sub-assembly containing an electrode and a base into which the electrode is embedded. It also includes an implantable package that has electronic components for providing electrical pulses to a patient's heart. The pacemaker also has a power supply and a flexible electrically conductive lead that connects the electronic components to the electrode. In addition to the pacemaker, the pacemaker system includes a removable insertion casing that is physically attached to the base portion of the electrode sub-assembly. Upon insertion of the pacemaker into a patient's heart, the pacemaker is detached from the removable insertion casing and deployed fully in the patient's chest.

Yet further, PCT publication number WO 22014182948 discloses a pacemaker system that comprises at least one pacemaker and that is, to a large extent, self-controlled, allows for long-term implantation in a patient, and minimizes inconveniences and problems associated with battery life. The document further discloses a mechanism in which at least two pacemakers are implanted in a patient, and in which the pacemakers communicate with each other at the time of a given pacing or respiratory event, without any required external input, and adjust pacing parameters to respond to the patient's need for blood flow. The document additionally discloses a design for a pacemaker in which the pacemaker electrode is connected to the pacemaker body by a lead that is configured to allow the pacemaker to lie parallel to the epicardial surface and to reduce stress on the pacemaker and heart tissue.

Other procedures are well known in the art that use insertion of catheters or implantation equipment through a sheath to access a tissue or organ of interest.

SUMMARY OF THE INVENTION

The present invention provides sheaths comprising structures that temporarily anchor the sheaths in a cavity, such as a pericardial sac, of a subject undergoing a medical procedure. The invention also provides sheath designs and methods for temporarily anchoring sheaths in cavities, such as a pericardial sac, of a subject such that the sheaths do not fall out of the space during a medical procedure. The present inventors previously developed an epicardial micropacemaker that relies on placement of an electrode at the epicardial surface via a sheath in the pericardial space. When the area of interest (such as the ablation focus or left atrial appendage) is remote from the site of entry into the pericardium with the sheath, there is generally only minimal concern that the sheath will fall out of the pericardial space during the pericardial procedure. In procedures that focus on cardiac features that are anatomically very close to the site of entry of the sheath, however, the sheath can fall out, requiring re-accessing the pericardial space with needle and wire (a procedure that in itself has significant risks). For example, with placement of the epicardial micropacemaker, the location of electrode implantation is just at the site of pericardial entry with the sheath. This makes positioning of the sheath at the target epicardial surface difficult due to concern for the sheath exiting the pericardial space.

The present invention provides an improvement on sheaths currently known in the art. The improvement lies in the sheath design, which includes structures that anchor the sheath in the relevant cavity by physically contacting the tissue that defines the cavity, including but not limited to the pericardium and the bladder, when deployed but are at the same time retractable such that the sheath can be removed without tearing the sac tissue.

BRIEF DESCRIPTION OF THE DRAWINGS

The accompanying drawings, which are incorporated in and constitute a part of this specification, illustrate embodiments of the invention, and together with the written description serve to explain certain principles of the invention.

FIG. 3 shows the loops of wires in their retracted state. FIG. 4 shows the loops of wires in their deployed state.

DETAILED DESCRIPTION OF VARIOUS EMBODIMENTS OF THE INVENTION

Figure 1:
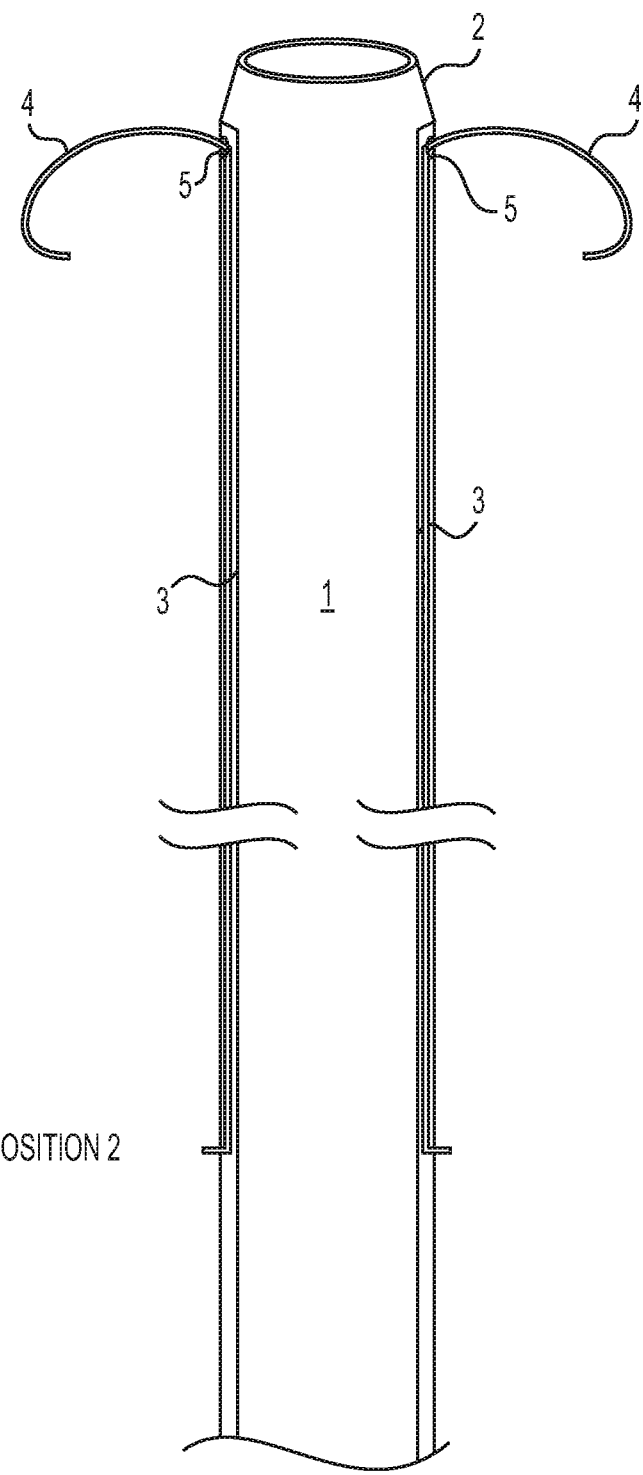
FIG. 1 is a drawing showing the general concept of the invention, where two wire anchors are deployed.

Reference will now be made in detail to various exemplary embodiments of the invention, examples of which are illustrated in the accompanying drawings. It is to be understood that the following discussion of exemplary embodiments is not intended as a limitation on the invention, as broadly disclosed herein. Rather, the following discussion is provided to give the reader a more detailed understanding of certain aspects and features of the invention.

Before embodiments of the present invention are described in detail, it is to be understood that the terminology used herein is for the purpose of describing particular embodiments only, and is not intended to be limiting. Unless defined otherwise, all medical, technical, and scientific terms used herein have the same meaning as commonly understood by one of ordinary skill in the art to which the term belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited. The present disclosure is controlling to the extent it conflicts with any incorporated publication.

As used herein and in the appended claims, the singular forms "a", "an", and "the" include plural referents unless the context clearly dictates otherwise. Thus, for example, reference to "a sheath" includes a plurality of such sheaths and reference to "a wire" includes reference to one or more wires and equivalents thereof known to those skilled in the art, and so forth. Furthermore, the use of terms that can be described using equivalent terms include the use of those equivalent terms. Thus, for example, the use of the term "subject" is to be understood to include the terms "patient", "human", "non-human animal", and other terms used in the art to indicate one who is subject to a medical treatment.

As discussed above, the invention relates to a new sheath design in which retractable wire anchors are embedded within or are an integral part of a sheath wall. The wire anchors are deployable to stabilize a sheath within a bodily space during, and where desired, after insertion of the sheath into the space. The wire anchors improve the likelihood that a sheath will not become dislodged from the space while a medical procedure is being performed. The invention further relates to methods of using the sheath to surgically access a tissue contained within the space or sac, such as epicardial tissue of a subject's heart, methods of enhancing surgical techniques and improving surgical outcomes by using the sheath, deploying the wire anchors during surgery, and retracting the wire anchors when stabilization of the sheath is no longer necessary. Additionally, the invention relates to methods of making a sheath of the invention by fabricating a sheath having channels disposed in the sheath wall and placing anchor wires within the channels such that the anchor wires can be deployed and retracted by pushing the wires out through openings in the distal portion of the sheath.

Figure 2:
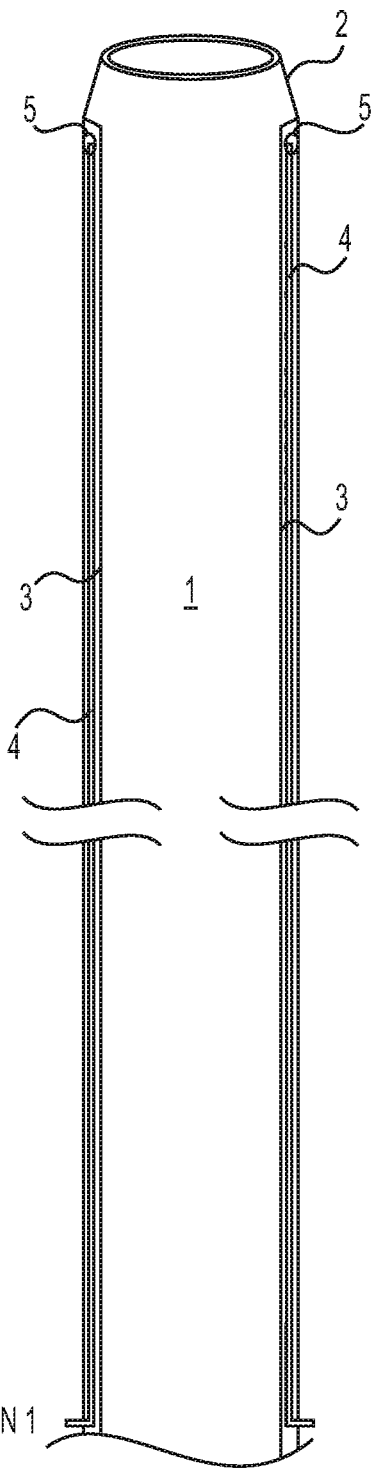
FIG. 2 is a drawing showing the sheath of FIG. 1, where the two wires are retracted back into the wall of the sheath.

FIGS. 1 and 2 depict the general concept of the invention. Sheath 1 comprises a sheath wall 2 into which channels 3 are built. Wire anchors 4 having a pre-formed curved or bent distal portion are inserted into channels 3. It is to be understood that the wire anchors are fabricated from a memory-shape or superelastic material, such as nitinol (a nickel-titanium alloy), other metal alloys, such as brass (zinc-copper) and gold-cadmium alloys, to name a few. The memory-shape or superelastic material is not restricted to metals, but instead can be any memory-shape or superelastic material, including shape-memory polymers (SMPs), certain thermoset polymers, and certain thermoplastics, for example. Those of skill in the art are well aware of memory-shape or superelastic materials; therefore, and exhaustive list is not required to be disclosed herein for the skilled artisan to make and use the invention.

The proximal end of wire anchors 4 is controlled by the operator (and is outside of the body during surgery) while the distal end can be advanced out of sheath wall 2 when positioning inside the space (e.g., pericardium) has occurred. Once advanced out of the distal sheath wall 2 through deployment hole 5 (by pushing/sliding forward the proximal side of the wire anchors 4; FIG. 1, "Position 2"), wire anchors 4 regain their "normal" shape and prevent the distal end of the sheath from being pulled back out of the space. When the proximal side is pulled/slid backwards, wire anchors 4 return to channels 3, and sheath 1 can be advanced or retracted without restriction (FIG. 2 "Position 1"). In certain embodiments wire anchors 4/channels 3 are symmetrically distributed around the cross-section of sheath 1. Any number of symmetrically distributed channels 3 can be used (e.g., 2, 3, 4, etc.).

Figure 3:
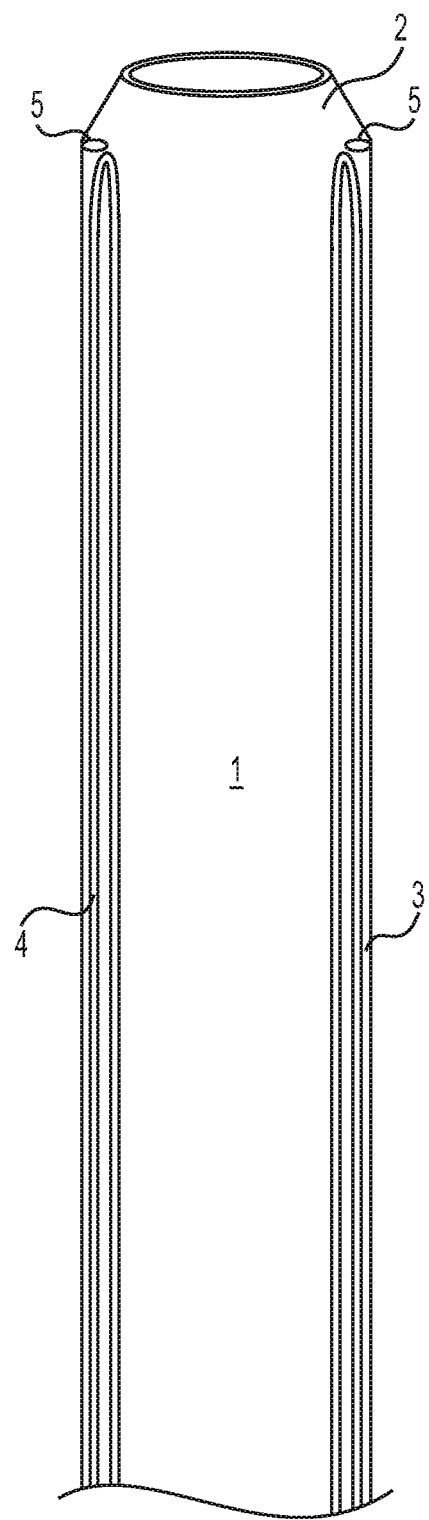
FIGS. 3 and 4 are drawings of the sheath of FIGS. 1 and 2, in which the wire anchors are formed in a loop shape.
Figure 4:
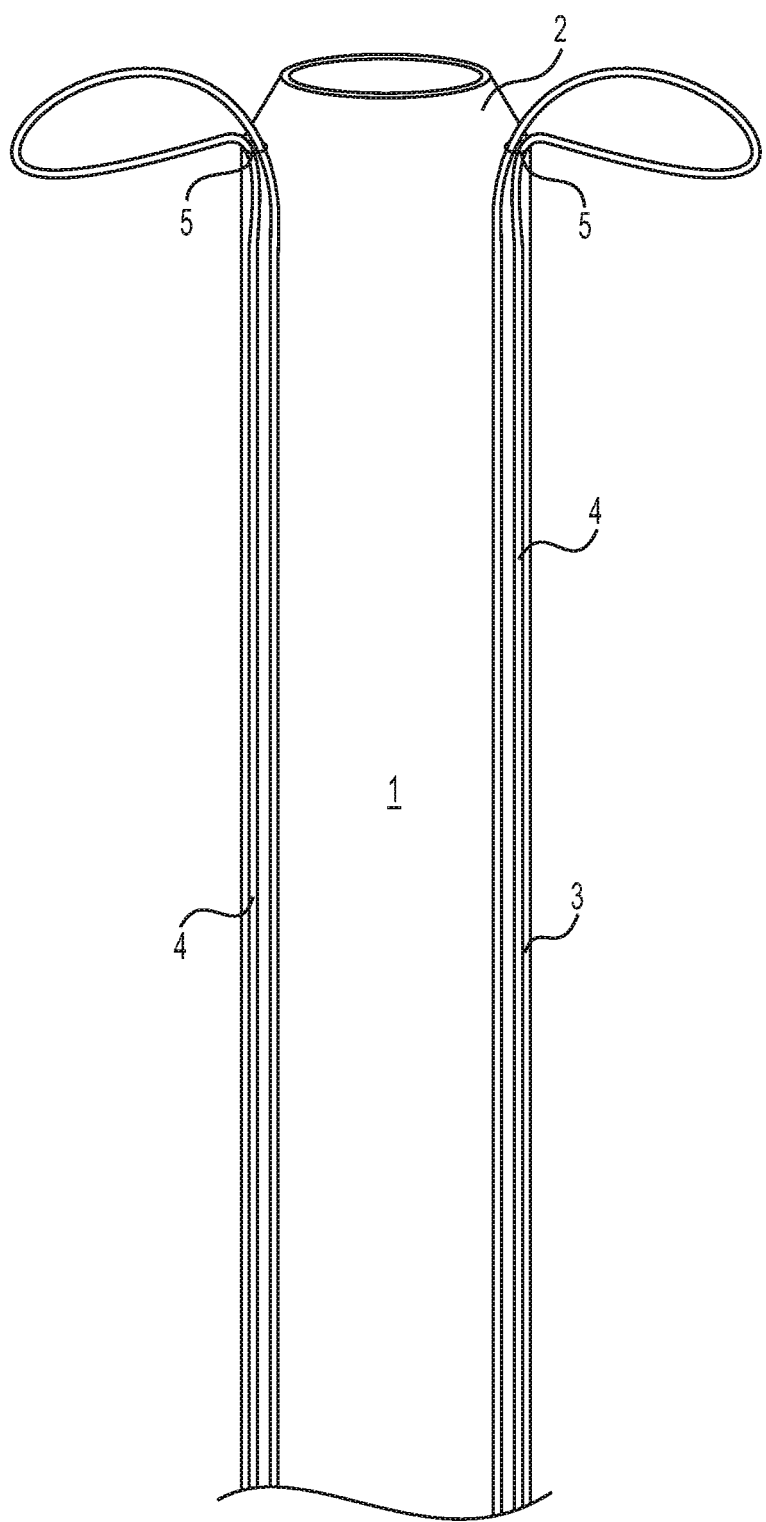
Figure 5:
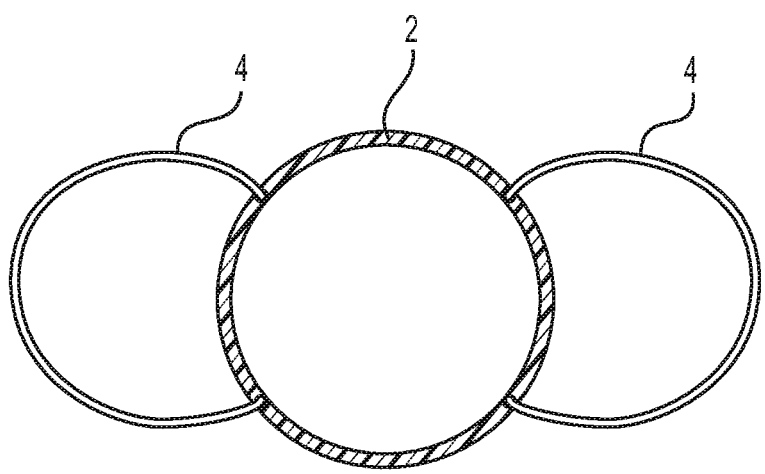
FIG. 5 shows a cross-section from the distal end of the sheath of FIG. 4 when deployed.
Figure 6:
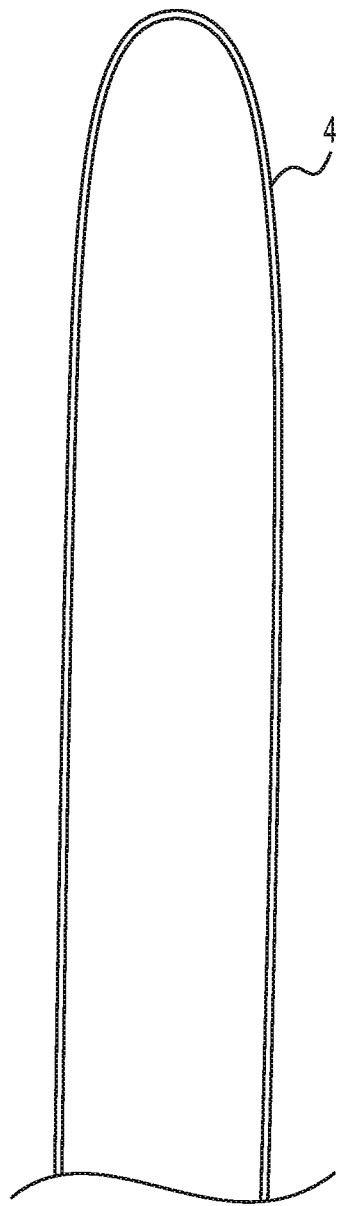
FIG. 6 shows the configuration of the wire loop anchors of FIGS. 3-5 while retracted within the sheath wall.

The invention also includes the concept depicted in FIGS. 3-6. The concept includes fabricating a wire anchor 4 out of a memory-shape material and/or superelastic material, and introducing two bends or curves at equidistant points from the center (along the length) of wire anchor 4 to form a looped wire anchor 4. The bends or curves are introduced such that they pre-form a looped wire anchor 4 to have a central section that projects away from the plane of the remaining portion of looped wire anchor 4. The angle of deflection of the center portion when exiting the sheath can be any angle, but is typically from about or exactly 10° to about or exactly 135°, such as about or exactly 20°, about or exactly 30°, about or exactly 45°, about or exactly 60°, about or exactly 90°, and about or exactly 120°. Looped wire anchor 4 also can include a pre-formed bend at the center of looped wire anchor 4, along the plane of the majority of looped wire anchor 4, to pre-form the loop structure. In one embodiment, one end of looped wire anchor 4 is inserted into a channel 3 at the distal end of sheath 1 and the other end of looped wire anchor 4 is inserted into an adjacent channel 3 at the distal end of sheath 1. The ends of looped wire anchor 4 are inserted through deployment hole 5. Looped wire anchor 4 is caused to move through channels 3 using mechanical force until looped wire anchor 4 is fully in place within channels 3. It is to be noted that deployment hole 5 is of sufficient width to allow the loop section to be inserted into channels 3 without the loop section being exposed beyond sheath wall 2. In another embodiment, a loop of looped wire anchor 4 is inserted into a single, wide channel 3 such that looped wire anchor 4 lays against the sides of channel 3. As with the previous embodiment, looped wire anchor 4 can have a pre-formed bend at its central section to cause a loop to form or, alternatively, the pressure induced by placement in channel 3, and the retention of the remaining, non-deployed portion of looped wire anchor 4 causes the loop structure to form. In accordance with the general disclosure of the invention, an operator (i.e., surgeon) can deploy the looped wire anchor 4 by pushing/sliding looped wire anchor 4 forward toward the distal end of sheath 1 through channel(s) 3, then retract it by pulling/sliding looped wire anchor 4 back proximally. FIG. 3 shows the sheath in an un-deployed or retracted state while FIGS. 4 and 5 show the sheath in a deployed state. As stated above, multiple looped wire anchors 4 can be disposed within sheath wall 2, and the channels 3 holding looped wire anchors 4 can be symmetrically distributed around the cross-section of sheath 4. Two loops are demonstrated in FIGS. 3, 4, 5, but the invention is not limited to any particular number of channels 3.

Figure 7:
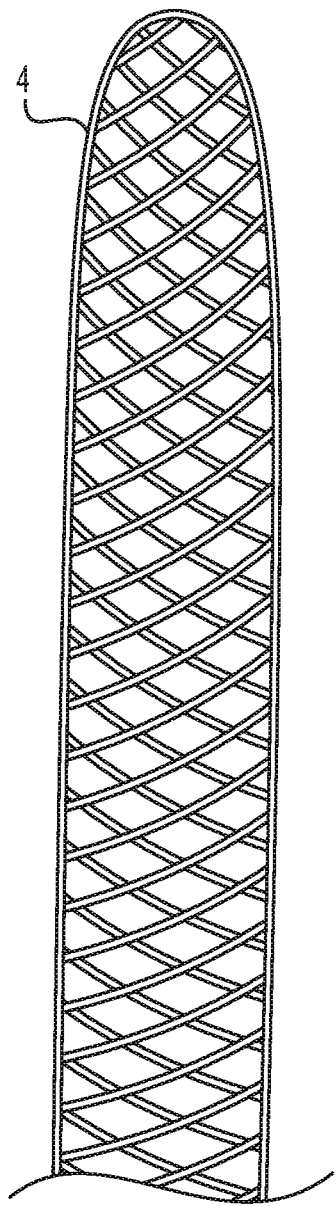
FIG. 7 shows the wire loop anchor of FIG. 6 when fabricated in a mesh.
Figure 8:
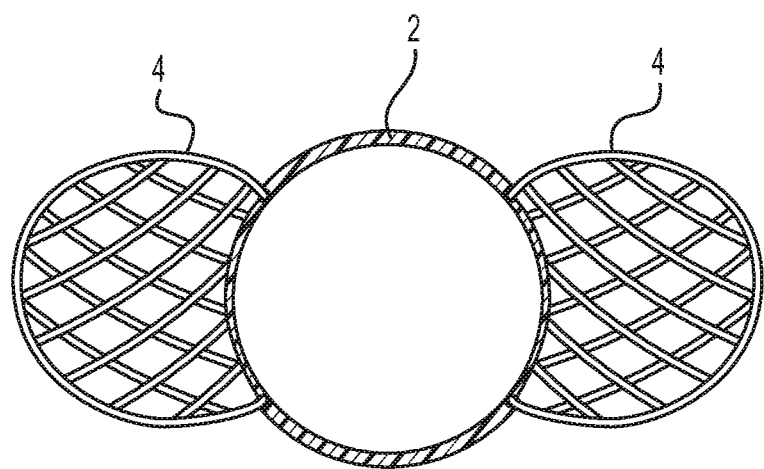
FIG. 8 shows a cross-section from the distal end of the sheath having the mesh loop anchor of FIG. 7 when deployed.

In another embodiment, a mesh-work of preformed wires is placed inside rectangular long channels 3 inside sheath wall 2, as discussed immediately above with regard to the second embodiment described. The mesh-work of preformed wires forms a looped wire anchor 4 in the same manner as described above, but provides more surface area for looped wire anchor 4 to interact with the tissue of the sac (e.g., pericardium). The mesh-work looped wire anchor 4 is depicted schematically in FIGS. 7 and 8. As with other embodiments, channels 3 can be symmetrically distributed around the cross-section of sheath 1 (i.e., 2, 3, 4, or any number of symmetrically distributed channels can be used; two mesh-work loop wire anchors are demonstrated in FIG. 8). In addition, in accordance with the disclosure above, pre-formed curves or bends can be introduced into mesh-work looped wire anchor 4 as well as a pre-formed loop at the central portion of mesh-work looped wire anchor 4.

With any of these configurations, the operator is able to actively advance or withdraw wire anchors 4 from the proximal end of the sheath in order to secure or release the distal tip of sheath 1 in the desired space (e.g., pericardium), respectively.

Deployment hole 5 can be positioned at the very distal end of sheath 1. Alternatively, deployment hole 5 can be positioned just proximal to the very distal end (e.g., proximal of the end of the sheath bevel, as shown in FIGS. 1, 2, 3, and 4) in order not to impede entry of the sheath over a dilator during initial sheath placement in the space of interest (e.g., pericardial space).

In the embodiments depicted and described with respect to FIGS. 1-8, the ability to pull on sheath 1 when it is in the deployed position allows separation of the sac from the organ or tissue it surrounds (e.g., the pericardium from the epicardium) and can facilitate the medical procedure being performed. This is advantageous for the epicardial micropacemaker discussed above, whereby sheath 1 can be pulled on during and after device deployment in order to allow space for the pacemaker to be deployed out of sheath 1 and into the pericardial space after the electrode has been implanted. Additionally, the ability to separate the pericardium (or other sac) from the epicardium (or other tissue surrounded by the sac) can allow for the placement of imaging equipment (such as a fiberoptic scope) for imaging inside the space during these procedures.

Figure 9:
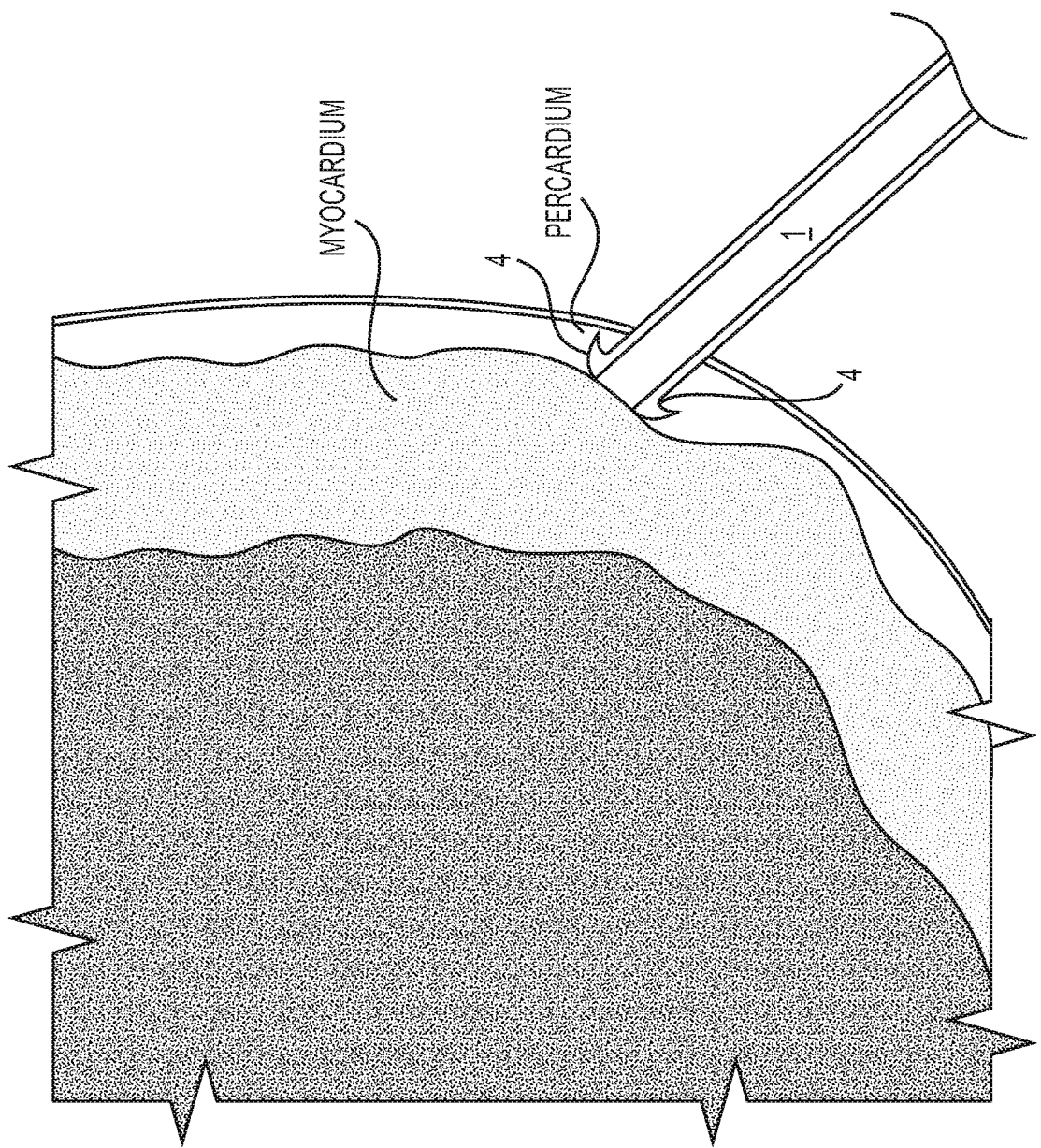
FIG. 9 depicts an embodiment of the invention where the anchors are hinges or hooks that are integral to the sheath wall.
Figure 10A:
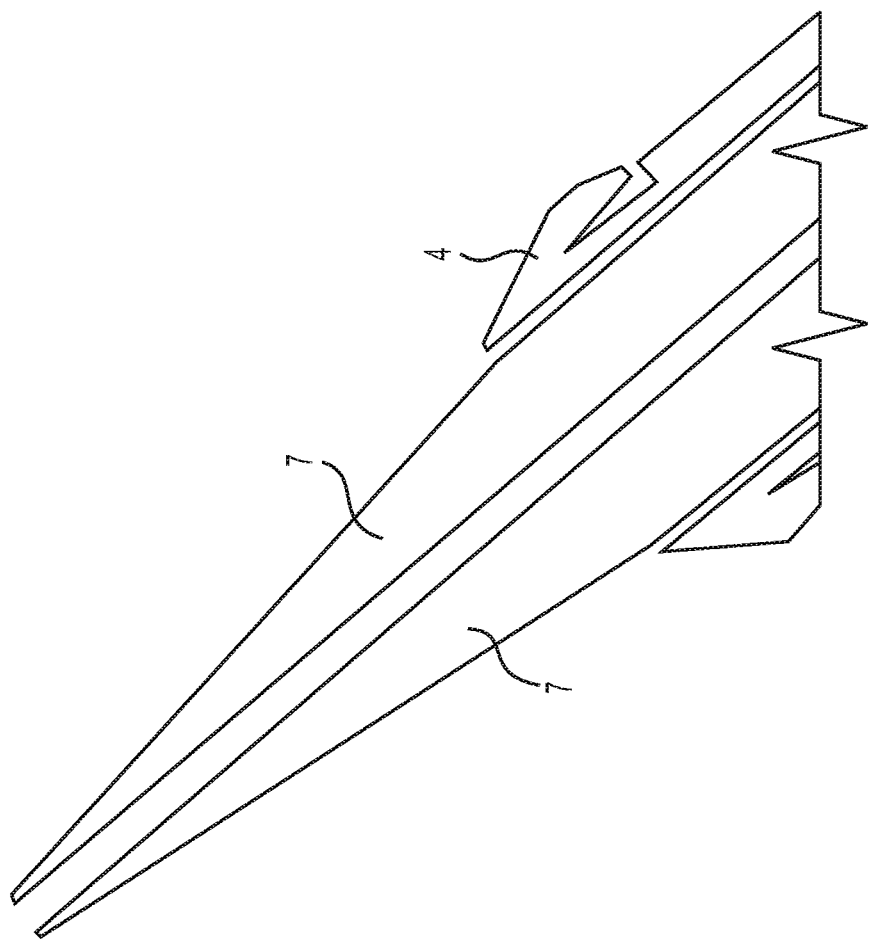
FIG. 10A shows the sheath of the invention in which a dilator is within the sheath lumen, forcing the hinges to lie flat against the exterior surface of the sheath.
Figure 10B:
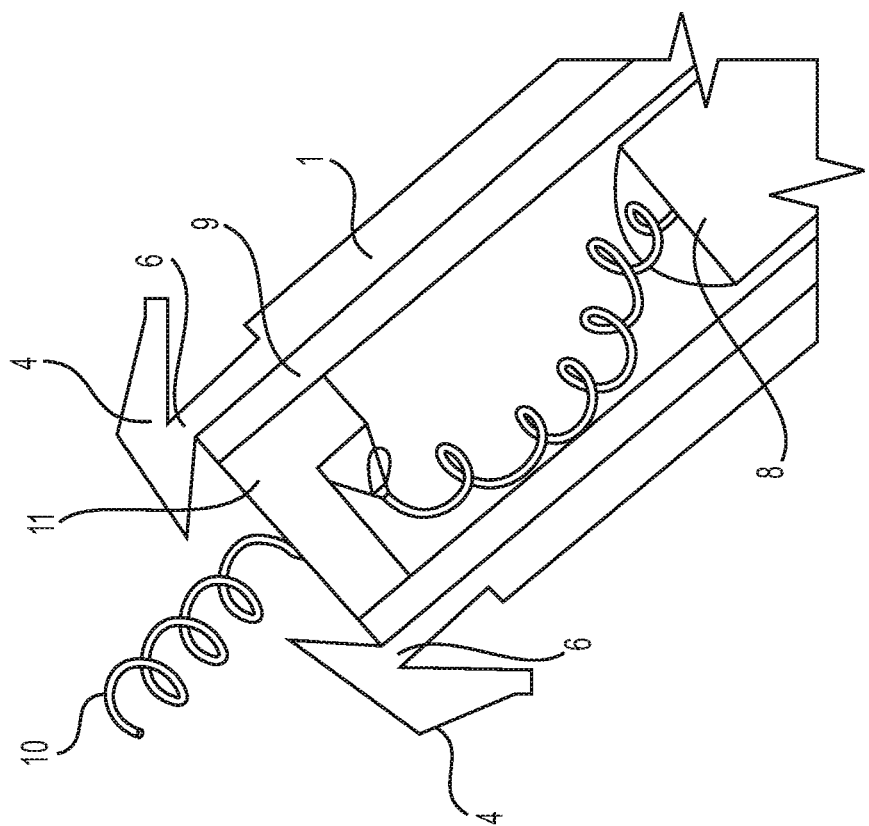
FIG. 10B shows the sheath of FIGS. 9 and 10A in which the dilator is removed, allowing the hinge anchors to deploy.

In another embodiment, anchor 4 is provided in the form of movable "hooks" that comprises "spring hinges" 6 that are built into the distal tip of sheath 1. An example of this embodiment is depicted in FIGS. 9 and 10. When a dilator 7 (or other space-occupying catheter/implantation equipment) is advanced beyond the distal tip of sheath 1, spring hinges 6 are bent so that anchor 4 lies flush with the outer surface of sheath wall 2 (as depicted in FIG. 10A). As a result, sheath 1 can freely be moved into or out of the space between the sac and the tissue it covers. When dilator 7 is removed and nothing occupies the sheath lumen, spring hinges 6 bend so that anchors 4 extend outwards (as depicted in FIG. 10B). As a result, sheath 1 cannot be removed from the space when the sheath lumen is empty (as depicted in FIG. 9). Note, for the anchor spring hinge design, implantation of an epicardial micropacemaker 8 is still possible despite the fact that the implantation equipment may occupy the sheath lumen during the procedure. After sheath 1 and dilator 7 are advanced into the space (see FIG. 10A), dilator 7 is removed, resulting in the tip being in the "secured" or "deployed" position in which anchor 4 extends away from sheath wall 2 (see FIG. 10B). Sheath 1 can then be easily manipulated without exiting the space until the distal tip is able to be pushed up against the tissue of interest. At that time, with pressure held on the tissue, the implantation equipment can be inserted such that even if anchor 4 is in the "released" or "retracted" position (see FIG. 10A), the steady pressure on the tissue by the surgeon prevents sheath 1 from falling out of the space. For example, after the electrode of micropacemaker 8 is implanted, micropacemaker 8 can be released and sheath 1 can exit the space.

In embodiments relating to a pacemaker system developed by the present inventors and described above (and exemplified in FIG. 10B), the pacemaker system comprises a pacemaker 8, an electronics package (not depicted), a flexible lead and a corkscrew electrode 10 protruding from a disc 11, all contained within an implantation housing 9 that passes through sheath 1. Disc 11 is lodged into the distal end of implantation housing 9, which is pushed up to but not past the inward lever arms of anchors 4. In this position, as illustrated in FIG. 10B, corkscrew electrode 10 can be affixed into the myocardium while sheath 1 is held within the pericardium by anchors 4. After electrode 10 is seated, the entire pacemaker system is extruded from sheath 1 and implantation housing 9 and into the pericardial space. Implantation housing 9 can then be advanced past the inward lever arm of each anchor 4, thereby bending spring hinge 6 so that anchor 4 lies flush with outer sheath wall 2. When all anchors 4 have thus been retracted, sheath 1 and inner sheath may be withdrawn, leaving the pacemaker system deployed in the pericardial space.

It will be apparent to those skilled in the art that various modifications and variations can be made in the practice of the present invention and in construction of the device without departing from the scope or spirit of the invention. Other embodiments of the invention will be apparent to those skilled in the art from consideration of the specification and practice of the invention. It is intended that the specification and drawings be considered as exemplary only, with a true scope and spirit of the invention being indicated by the following claims.

The invention claimed is:

1. A sheath for implanting a medical device or medical equipment into a body cavity of a patient, said sheath comprising:

a sheath wall extending from a proximal portion to a distal portion of the sheath, the sheath wall comprising one or more channels disposed within the sheath wall that traverse the sheath wall in a direction from the proximal portion to the distal portion of the sheath,
wherein:
the one or more channels terminate adjacent the distal portion of the sheath with a first opening located below the distal portion of the sheath through which a distal tip of a wire anchor can be extended and retracted,
the one or more channels terminate at or adjacent to the proximal portion of the sheath with a second opening through which a proximal portion of the wire anchor can be manipulated by an operator to extend and retract the wire anchor from and into the first opening,
the sheath is configured to be inserted through a wall of the body cavity so that the distal portion of the sheath and the first opening are located inside the body cavity above an inner surface of the wall of the body cavity,
the wire anchor is comprised of a memory-shape material or superelastic material that is pre-formed to comprise a curve or bend that is caused to straighten when disposed within the one or more channels, but allowed to reform its pre-formed curved or bent shape when not disposed within the one or more channels so that the wire anchor extends from the first opening initially in a first direction upward towards the distal portion of the sheath, but then curls downwards in an opposite second direction to engage the inner surface of the wall enclosing the body cavity as the operator pushes the proximal portion of the wire anchor at the second opening to push the distal tip of the wire anchor out of the first opening thus forming a wire anchor providing an anchoring function for the sheath on the inner surface of the wall that retains the distal portion of the sheath spaced above the inner surface of the wall within the body cavity by contact of the wire anchor with the inner surface of wall of the body cavity, and
retraction of the wire anchor, by the operator pulling on the proximal portion of the wire anchor at the second opening, into the one or more channels of the sheath wall disables the anchoring function and allows removal of the sheath without tearing tissue of the inner surface of the wall of the body cavity that the wire anchor was anchored to.

2. The sheath of claim 1, wherein the wire anchor is a single wire having a curve or bend that, when extended from the sheath wall, extends away from the sheath at about 10° to about 135° from the wall surface.

3. The sheath of claim 2, wherein the wire anchor extends away from the sheath at about 90°.

4. The sheath of claim 1, wherein the wire anchor comprises nitinol.

5. The sheath of claim 1, wherein the wire anchor comprises a thermoplastic or a thermoset polymer.

6. The sheath of claim 1, wherein the wire anchor is a single wire that comprises a loop structure at a central point of the wire anchor, and wherein the curve or bend comprises two curves or bends equidistant from the central point of the wire anchor that, when the wire anchor is extended from the one or more channels, cause the wire anchor to extend away from the sheath at approximately 90° from the inner surface of the wall.

7. The sheath of claim 6, wherein the wire anchor comprises a mesh structure connecting one side of the loop structure to another side of the loop structure.

8. The sheath of claim 1, wherein the body cavity comprises a pericardial space defined by a pericardium.

9. The sheath of claim 1, wherein:
the wire anchor is a single wire that comprises a loop structure at its central point, and
the wire anchor includes a preformed curved distal portion that comprises two curves equidistant from the central point of the wire anchor that have a central section that projects away from a plane of a remaining portion of the looped wire anchor.

10. The sheath of claim 1, wherein the wire anchor is a single wire that includes a preformed curved distal portion which, when the preformed curved distal portion is extended from the first opening in the sheath wall, comprises a single curve.

11. A sheath for implanting a medical device or medical equipment into a body cavity of a patient, said sheath comprising:
a sheath wall comprising at least one anchoring element disposed at a distal tip of the sheath, said anchoring element including a distal tip and a proximal tip,
wherein:
said anchoring element is in a form of a hinge or hook,
said sheath wall is comprised of a memory-shape material or superelastic material that is pre-formed to cause the proximal tip of the hinge or hook to extend from a generally cylindrical surface of the sheath wall when not forced to remain substantially in a same shape as a remaining portion of the sheath wall by pressure exerted on the distal tip of the hinge or hook by a structure disposed within a lumen of the sheath,
extension of the hinge or hook away from the generally cylindrical surface of the sheath wall creates an anchor having an anchoring function that retains the distal tip of the sheath within the body cavity by contact of the anchor with a surface of the body cavity while simultaneously extending the distal tip of the hinge or hook inwardly to extend over an opening of the lumen at the distal tip of the sheath, and
contact of a mechanical element of sufficient diameter into the lumen of the sheath causes retraction of the hinge or hook, thus disabling the anchoring function of the anchor and allowing removal of the sheath from the body cavity without tearing of the surface of the body cavity.

12. The sheath of claim 11, wherein the anchor comprises nitinol.

13. The sheath of claim 11, wherein the anchor comprises a thermoplastic or a thermoset polymer.

14. The sheath of claim 11, wherein the body cavity is a pericardial space.

15. A method of anchoring a sheath in a body cavity, comprising:
inserting the sheath through a wall of the body cavity so that a distal portion of the sheath is located in the body cavity,
wherein:
the sheath includes a sheath wall extending from a proximal portion to the distal portion of the sheath, the sheath wall comprising one or more channels disposed within the sheath wall that traverse the sheath wall in a direction from the proximal portion to the distal portion of the sheath, wherein the one or more channels terminate adjacent the distal portion of the sheath with a first opening located below the distal portion of the sheath through which a distal tip of a wire anchor can be extended and retracted, and wherein the one or more channels terminate at or adjacent to the proximal portion of the sheath with a second opening through which a proximal portion of the wire anchor can be manipulated by an operator to extend and retract the wire anchor from and into the first opening, wherein the sheath is configured to be inserted through a wall of the body cavity so that the distal portion of the sheath and the first opening are located inside the body cavity above an inner surface of the wall of the body cavity, and the wire anchor is comprised of a memory-shape material or superelastic material that is pre-formed to comprise a curve or bend that is caused to straighten when disposed within the one or more channels, but allowed to reform its pre-formed curved or bent shape when not disposed within the one or more channels, pushing the proximal portion of the wire anchor at the second opening so that the wire anchor extends from the first opening initially in a first direction upward towards the distal portion of the sheath, but then curls downwards in an opposite second direction to engage the inner surface of the wall enclosing the body cavity as the operator pushes the proximal portion of the wire anchor at the second opening to push the distal tip of the wire anchor out of the first opening thus forming a wire anchor providing an anchoring function for the sheath on the inner surface of the wall that retains the distal portion of the sheath spaced above the inner surface of the wall within the body cavity by contact of the wire anchor with the inner surface of wall of the body cavity, and retracting the wire anchor, by the operator pulling on the proximal portion of the wire anchor at the second opening, into the one or more channels of the sheath wall to disable the anchoring function and remove the sheath from the body cavity without tearing tissue of the inner surface of the wall of the body cavity that the wire anchor was anchored to.

16. The method of claim 15, wherein the body cavity is a pericardial space.

\* \* \* \* \*